United States Patent
Ceballos et al.

(10) Patent No.: US 6,522,915 B1
(45) Date of Patent: *Feb. 18, 2003

(54) SURROUND SHROUD CONNECTOR AND ELECTRODE HOUSINGS FOR A SUBCUTANEOUS ELECTRODE ARRAY AND LEADLESS ECGS

(75) Inventors: Thomas I. Ceballos, Spring Lake Park, MN (US); John E. Nicholson, Blaine, MN (US); Eric J. Panken, Edina, MN (US); James D. Reinke, Maple Grove, MN (US); James Strom, Arden Hills, MN (US); Kevin K. Tidemand, East Bethel, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/697,438

(22) Filed: Oct. 26, 2000

(51) Int. Cl.$^7$ ................................................ A61B 5/042

(52) U.S. Cl. ........................................ 600/509; 607/36

(58) Field of Search ............................. 607/36; 600/509

(56) References Cited

U.S. PATENT DOCUMENTS

| | | |
|---|---|---|
| 3,983,867 A | 10/1976 | Case |
| 4,023,565 A | 5/1977 | Ohlsson |
| 4,082,086 A | 4/1978 | Page et al. |
| 4,121,576 A | 10/1978 | Greensite |
| 4,170,227 A | 10/1979 | Feldman et al. |
| 4,263,919 A | 4/1981 | Levin |

(List continued on next page.)

FOREIGN PATENT DOCUMENTS

EP 0 534 782 9/1992

OTHER PUBLICATIONS

Barnes, A.R. et al., "Standardization of Precordial Leads" *The American Heart Journal*, Issue 15, 1938, pp. 235–239.

Burch, George E., M.D. and DePasquale, Nicholas P., M.D. *A History of Electrocardiography*, Year Book Medical Publishers, Inc., Copyright 1964, Library of congress Catalog Card No. 63:15511, 309 pp.

Einthoven, W., "Ueber die Form des menschlichen Electrocardiogramms" (German), *Arch f d Ges Physiol*, Issue 60, 1895, pp. 101–123.

Einthoven, W., "Nieuwe metehoden voor clinisch onderzoek (New Methods for Clinical Investigation)", *Ned T Geneesk*, vol. 29 II, 1893, pp. 263–286.

Matteucci, C., "Sur un phenomene physiologique produit par les muscles en contraction" *Ann Chim Phys*, Issue 6, 1842, pp. 339–341.

Sanderson, Burdon, "Experimental results relating to the rhythmical and excitatory motiuouns of the ventricle of the frog," *Proc R Soc Lond*, Issue 27, 1878, pp. 410–414.

*Primary Examiner*—Scott M. Getzow
(74) *Attorney, Agent, or Firm*—Girma Wolde-Michael; Paul H. McDowall

(57) ABSTRACT

The invention discloses a subcutaneous electrode array or SEA for use in medical devices. The arrangement provides an enhanced capability for detecting and gathering electrical cardiac signals via the array of relatively closely spaced subcutaneous electrodes. Further, switching circuits, signal processors and memory to process electric cardiac signals are implemented to enable a leadless orientation-insensitive SEA scheme for receiving the electrical signal from the heart. The SEA is distributed over the perimeter of the implanted medical device and includes a non-conductive surround shroud of biocompatible material. The surround shroud is placed around the periphery of the case of the implanted medical device. Various configurations of recesses, each of which contain individual electrodes, are implemented to provide an enhanced signal to noise ratio for improved signal quality.

10 Claims, 11 Drawing Sheets

U.S. PATENT DOCUMENTS

| | | |
|---|---|---|
| 4,310,000 A | 1/1982 | Lindemans |
| 4,313,443 A | 2/1982 | Lund |
| 4,476,868 A | 10/1984 | Thompson |
| 4,593,702 A | 6/1986 | Kepski et al. |
| 4,674,508 A | 6/1987 | DeCote |
| 4,729,376 A | 3/1988 | DeCote, Jr. |
| 5,052,388 A | 10/1991 | Sivula et al. |
| 5,331,966 A | 7/1994 | Bennett et al. |
| 5,345,362 A | 9/1994 | Winkler |
| 5,456,698 A * | 10/1995 | Byland et al. |
| 5,535,097 A | 7/1996 | Ruben et al. |

* cited by examiner

| CONFIGURATION | VECTOR 1 (LONGEST) | VECTOR 2 (SHORTEST) | VECTOR 3 |
|---|---|---|---|
| 2 ELECTRODES | 2.1" | NA | NA |
| 3 ELECTRODES ORTHOGONAL | 1.77" | 1.3" | NA |
| 3 ELECTRODES EQUAL SPACING | 1.7" | 1.7" | 1.7" |
| 4 ELECTRODES ORTHOGONAL | 2.10" | 1.83" | NA |

*TABLE 1*

| CONFIGURATION | MINIMUM | MEAN | MAXIMUM | STANDARD DEVIATION | UNITS |
|---|---|---|---|---|---|
| 2 ELECTRODES | 0 | 1.337 | 2.1 | 0.647 | mV |
| 3 ELECTRODES ORTHOGONAL | 1.048 | 1.398 | 1.77 | 0.237 | mV |
| 3 ELECTRODES EQUAL SPACING | 1.472 | 1.623 | 1.7 | 0.07 | mV |
| 4 ELECTRODES ORTHOGONAL | 1.381 | 1.774 | 2.1 | 0.209 | mV |

*TABLE 2*

SURROUND SHROUD CONNECTOR AND ELECTRODE HOUSINGS FOR A SUBCUTANEOUS ELECTRODE ARRAY AND LEADLESS ECGS

FIELD OF THE INVENTION

The present invention relates generally to implantable pacemakers and more particularly to a subcutaneous multiple electrode sensing and recording system for acquiring electrocardiographic data and waveform tracings from an implanted pacemaker without the need for or use of surface (skin) electrodes. More particularly, the present invention relates to implantable devices that are equipped with a compliant, insulative "shroud" into which are placed electrodes (a Subcutaneous Electrode Array or SEA) that, in turn, detect cardiac depolarizations communicable and displayable by a portable device programmer.

BACKGROUND OF THE INVENTION

The electrocardiogram (ECG) is commonly used in medicine to determine the status of the electrical conduction system of the human heart. As practiced the ECG recording device is commonly attached to the patient via ECG leads connected to pads arrayed on the patient's body so as to achieve a recording that displays the cardiac waveforms in any one of 12 possible vectors.

The history of the ECG dates back to 1842 when the Italian physicist, Carlo Matteucci discovered that each heartbeat was accompanied by a detectable electric signal (Matteucci C. *Sur un phenomene physiologique produit par les muscles en contraction. Ann Chim Phys* 1842;6:339–341). In 1878, two British physiologists, John Burden Sanderson and Frederick Page, determined that the heart signal consisted of, at least, two phases, the QRS (ventricular depolarization) and the repolarization or T-wave (Burdon Sanderson J. *Experimental results relating to the rhythmical and excitatory motions of the ventricle of the frog. Proc R Soc Lond* 1878;27:410–414). It was not until 1893, however, that Willem Einthoven introduced the term 'electrocardiogram' at a meeting of the Dutch Medical Association (Einthoven W: *Nieuwe methoden voor clinisch onderzoek [New methods for clinical investigation]*. Ned T Geneesk 29 II: 263–286, 1893), although he later disavowed he was the originator of the term. Einthoven may, however, be called the Father or electrocardiography, since he won the Nobel Prize for his achievements in 1924. It was he who finally dissected and named all of the cardiac waveforms (P, Q, R, S, T) that commonly appear on an ECG tracing from a 'normal' person (Einthoven W. *Ueber die Form des menschlichen Electrocardiogramms. Archf d Ges Physiol* 1895;60:101–123).

Einthoven and other medical practitioners of that time were aware of only three vectors (I, II, and III) that are achieved by placement of the ECG electrodes on specific body sites. The remaining nine sites were discovered later in the twentieth century. In 1938, American Heart Association and the Cardiac Society of Great Britain defined the standard positions (I–III) and wiring of the chest leads V1–V6. The 'V' stands for voltage. (Barnes AR, *Pardee HEB*, White PD. et al. *Standardization of precordial leads. Am Heart J* 1938;15:235–239). Finally, in 1942, Emanuel Goldberger added the augmented limb leads aVR, aVL and aVF to Einthoven's three limb leads and the six chest leads thereby creating the 12-lead electrocardiogram that is routinely used today for cardiac diagnostic purposes. A standard reference for further information on the history of electrocardiography is: *A History of Electrocardiography*, G. E. Burch and N. P, DePascuale, Norman Publishing, San Francisco.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) that currently requires externally attached electrodes and the electrogram (EGM) that requires implanted pacing leads. The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and. R-wave, the morphology of the P-wave and R-wave and the direction of propagation of the depolarization represented by the P-wave and R-wave in the heart. The detection, analysis and storage of such EGM data within implanted medical devices are well known in the art. Acquisition and use of ECG tracing(s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes available in or around the heart to pick up the depolarization wave front As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, in fact, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Unfortunately, surface electrodes have some serious drawbacks. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration or motion. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals and transform them into a tracing that is the same as or comparable to tracings obtainable via ECG leads attached to surface electrodes.

Previous art describes how to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems which combine surface EKG signals for artifact rejection.

The primary use for multiple electrode systems in the prior art is vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 to Page, et al., discloses a four electrode orthogonal array that may be applied to the patient's skin both for convenience and to ensure the precise orientation of one electrode to the other. U.S. Pat. No. 3,983,867 to Case describes a vector cardiography system employing ECG electrodes disposed on the patient in normal locations and a hex axial reference system orthogonal display for displaying ECG signals of voltage versus time generated across sampled bipolar electrode pairs.

U.S. Pat. No. 4,310,000 to Lindemans and U.S. Pat. Nos. 4,729,376 and 4,674,508 to DeCote, incorporated herein by reference, disclose the use of a separate passive sensing reference electrode mounted on the pacemaker connector block or otherwise insulated from the pacemaker case in order to provide a sensing reference electrode which is not part of the stimulation reference electrode and thus does not have residual after-potentials at its surface following delivery of a stimulation pulse.

Moreover, in regard to subcutaneously implanted EGM electrodes, the aforementioned Lindemans U.S. Pat. No. 4,310,000 discloses one or more reference sensing electrode positioned on the surface of the pacemaker case as described above. U.S. Pat. No. 4,313,443 issued to Lund describes a subcutaneously implanted electrode or electrodes for use in monitoring the ECG.

Finally, U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

SUMMARY OF THE INVENTION

The present invention encompasses a leadless Subcutaneous Electrode Array (SEA) that provides various embodiments of a compliant surround shroud into which are placed electrodes embedded into recesses in the surround that is attached to the perimeter of the implanted pacemaker. These electrodes are electrically connected to the circuitry of the implanted pacemaker and detect cardiac depolarization waveforms displayable as electrocardiographic tracings on the pacemaker Programmer screen when the programming head is positioned above an implanted pacemaker (or other implanted device) so equipped with a leadless SEA.

The present invention provides a method and apparatus that may be implemented into the aforementioned medical devices to provide an enhanced capability of detecting and gathering electrical cardiac signals via an array of relatively closely spaced subcutaneous electrodes (located in a shroud placed circumferentially on the perimeter of an implanted device) which may be employed with suitable switching circuits, signal processors, and memory to process the electrical cardiac signals between any selected pair or pairs of the electrode array in order to provide a leadless, orientation-insensitive means for receiving the electrical signal from the heart.

The compliant surround shroud may consist of a non-conductive, bio-compatible urethane polymer, silicone, or softer urethane that retains its mechanical integrity during manufacturing and prolonged exposure to the hostile environment of the human body. The surround shroud placed around the perimeter of the pacemaker case of the subcutaneously implanted medical device has two preferred embodiments, the first with four and the second with three recesses, each of which contains an individual electrode. The four-electrode embodiment provides a better signal-to-noise ratio that the three-electrode embodiment. Embodiments, using a single electrode pair, are very sensitive to appropriate orientation of the device during and post implantation. Embodiments, using more than four electrodes increase complexity without any significant improvement in signal quality.

The preferred perimeter embodiment has electrodes connected to two amplifiers that are hardwired to two electrode pairs that record simultaneous ECGs. These ECGs are stored and sorted for processing in the pacemaker's microprocessor. An alternative embodiment has electrodes on the face of the lead connector and/or face of the pacemaker that may be selectively or sequentially coupled in one or more pairs to the terminals of one or more sense amplifiers to pick up, amplify and process the electrical cardiac signals across each electrode pair. In one embodiment, the signals from the selected electrode pairs may be stored and compared to one another in order to determine the sensing vector that provides the largest cardiac signal (in a test mode). Following completion of the test mode, the system may employ the selected subcutaneous ECG signal vector for a number of applications.

The surround shroud and the electrode recesses are easy-to-mold. Since they also are better able to stand up to heat stress, they are easy to manufacture. The preferred perimeter embodiment (with four electrodes and two amplifiers) has several advantages. Since fewer amplifiers are needed, this embodiment saves power, thus extending battery life. The preferred embodiment also requires less memory, thereby allowing smaller electronic circuitry that can be manufactured less expensively.

Previous art found in U.S. Pat. No. 5,331,966 had electrodes placed on the face of the implanted pacemaker. When facing muscle, the electrodes were apt to detect myopotentials and were susceptible to baseline drift. The present invention minimizes myopotentials and allows the device to be implanted on either side of the chest by providing maximum electrode separation and minimal signal variation due to various pacemaker orientations within the pocket because the electrodes are placed on the surround shroud in such a way as to maximize the distance between electrode pairs.

The spacing of the electrodes in the present invention provides maximal electrode spacing and, at the same time, appropriate insulation from the pacemaker casing due to the insulative properties of the compliant shroud and the cup recesses into which the electrodes are placed. The electrode placement maintains a maximum and equal distance between the electrode pairs. Such spacing with the four-electrode embodiment maintains the maximum average signal due to the fact that the spacing of the two vectors is equal and the angle between these vectors is 90°, as is shown in mathematical modeling. Such orthogonal spacing of the electrode pairs also minimizes signal variation. An alternate three-electrode embodiment has the electrodes arranged within the surround shroud in an equilateral triangle along the perimeter of the implanted pacemaker. Vectors in this embodiment can be combined to provide adequate sensing of cardiac signals (ECGs).

Previous art ('966) had no recesses for the electrodes and, hence, made the device susceptible to motion detection. The present invention may recess the electrodes below the surface of the shroud, thereby eliminating interface with the body tissue, thus minimizing or eliminating motion artifact. An alternative embodiment, which provides an open cover for the electrodes and allows body fluids to come into contact with the electrode while minimizing the fluid movement, further enhances this effect. These covers also provide protection for the electrodes, so as to prevent damage during the implant procedure. The electrode covers also prevent contact with any other implanted devices which may be placed in the same pocket, as well as protection against any electro surgical electrodes used during the implant or explant procedures.

The electrodes' surfaces require protection during handling as well as to prevent contamination. A coating, such as may be provided by Dexamethazone Sodium Phosphate, NaCL (salts) and sugar solutions, provides such protection as well as enhancing the wetting of the electrode surface after implant. Conductive hydro gels, applied wet and allowed to dry, may also be applied to the electrode surfaces to protect them from damage during handling and prevent contamination.

The present invention allows the physician or medical technician to perform leadless follow-up that, in turn, eliminates the time it takes to attach external leads to the patient. Such time savings can reduce the cost of follow-up, as well as making it possible for the physician or medical technician to see more patients during each day. Though not limited to these, other uses include: Holter monitoring with event storage, arrhythmia detection and monitoring, capture detection, ischemia detection and monitoring (S-T elevation and depression on the ECG), changes in QT interval, and transtelephonic monitoring.

Table 1 illustrates four possible electrode sites on the compliant surround shroud.

Figure 8:
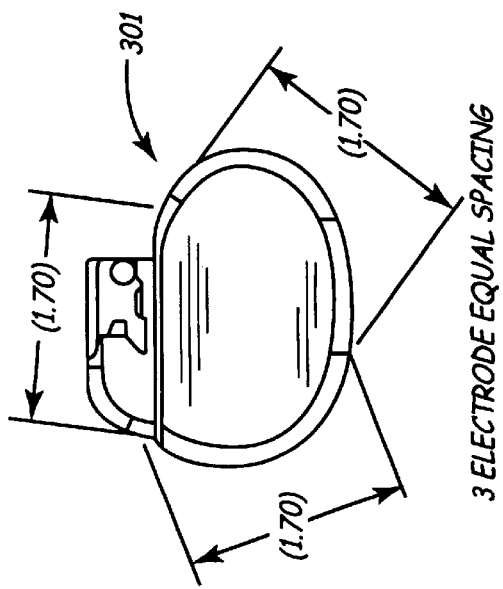
Figure 8:
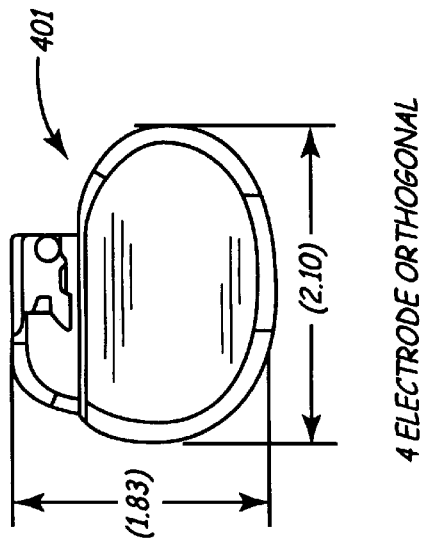
Figure 8:
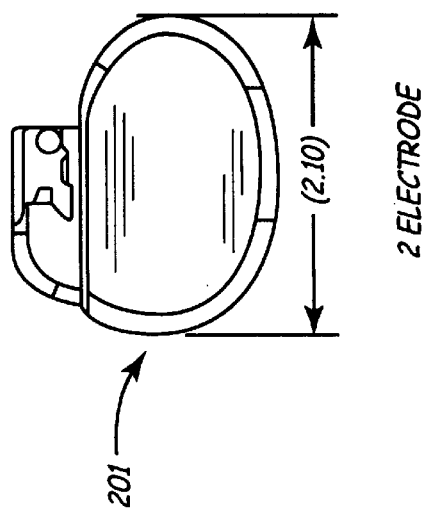
Figure 8:
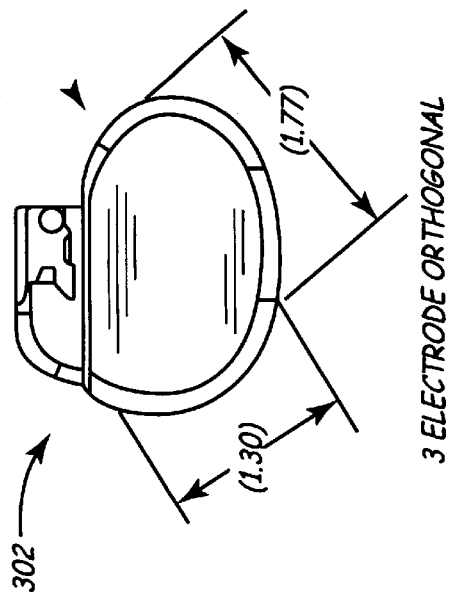

FIG. 8 is an illustration of the various possible electrode sites that may be located along the compliant surround shroud.

Figure 7:
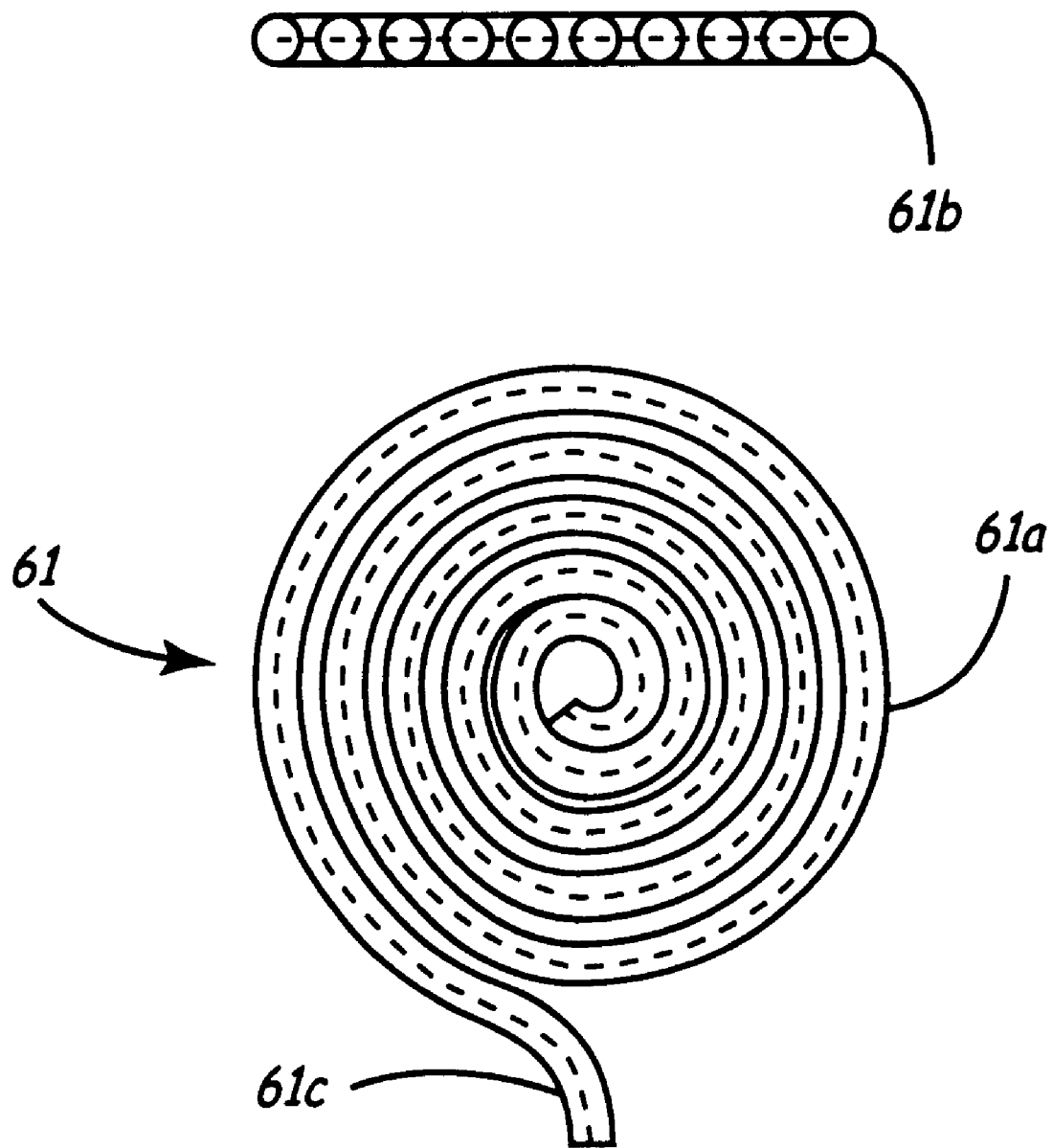
FIG. 7 is a cross sectional view of a helical coil, which is one embodiment of an electrode practiced in the present invention.

Table 2 provides the resultant signal amplitudes attained when using the electrode sites given in Table 1 and FIG. 7.

Figure 9:
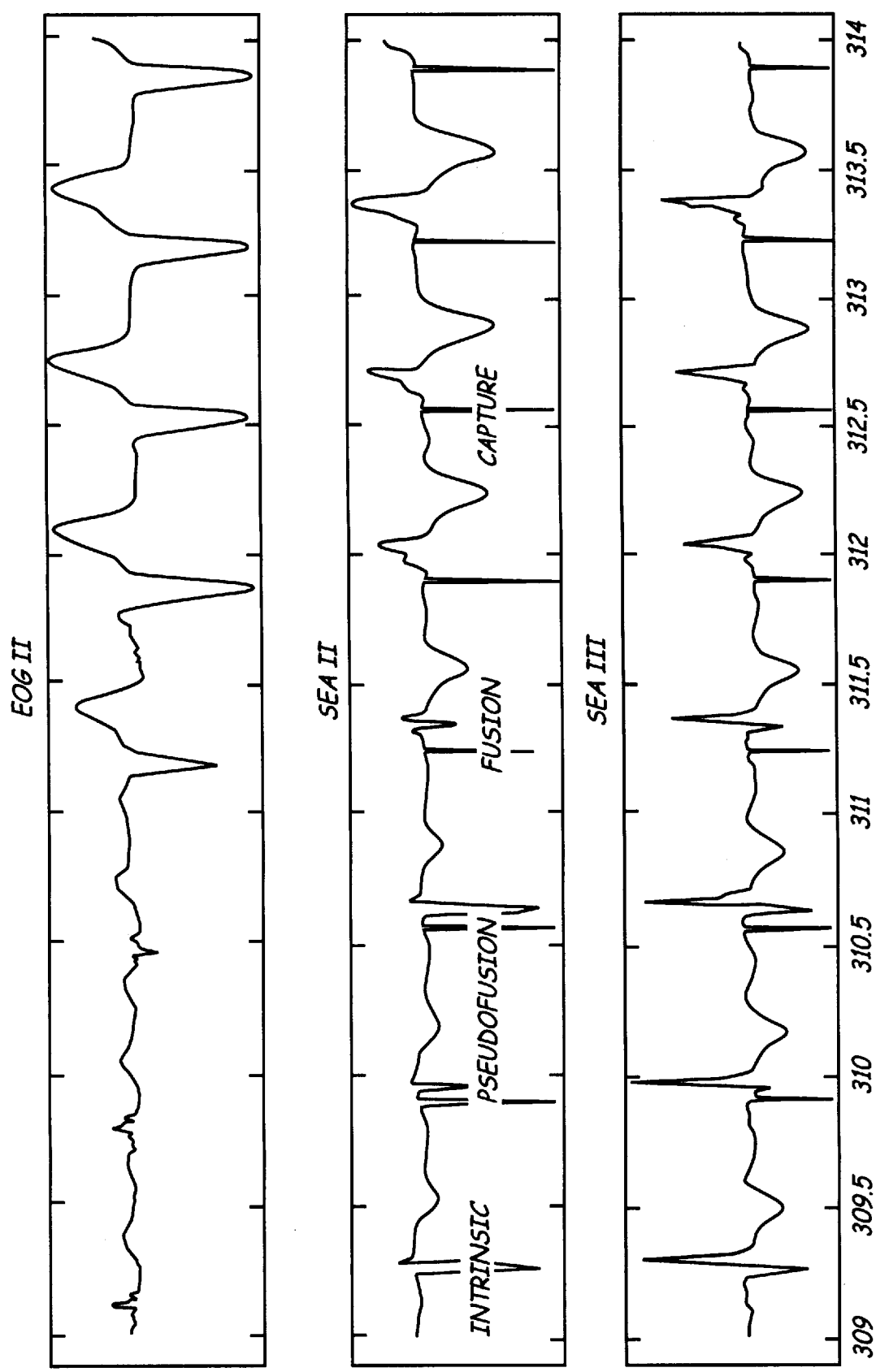

FIG. 9 is a display of three ECG tracings, one from surface electrodes, and the remaining two from the SEA.

DETAILED DESCRIPTION OF THE DRAWINGS

Figure 1:
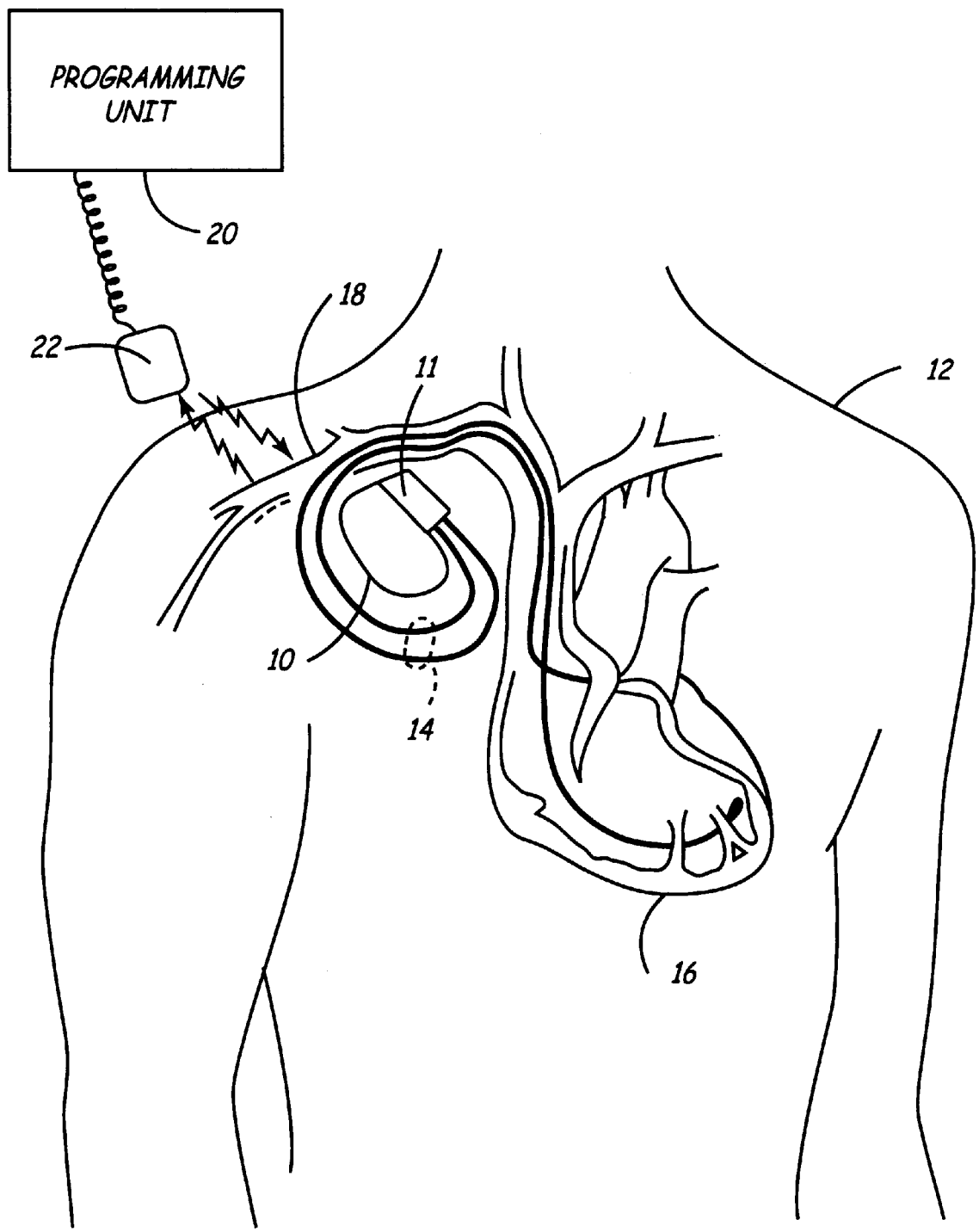
FIG. 1 is an illustration of a body-implantable device system in accordance with one embodiment of the invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker in this embodiment—which has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed. generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components, such as may occur during transtelephonic monitoring.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
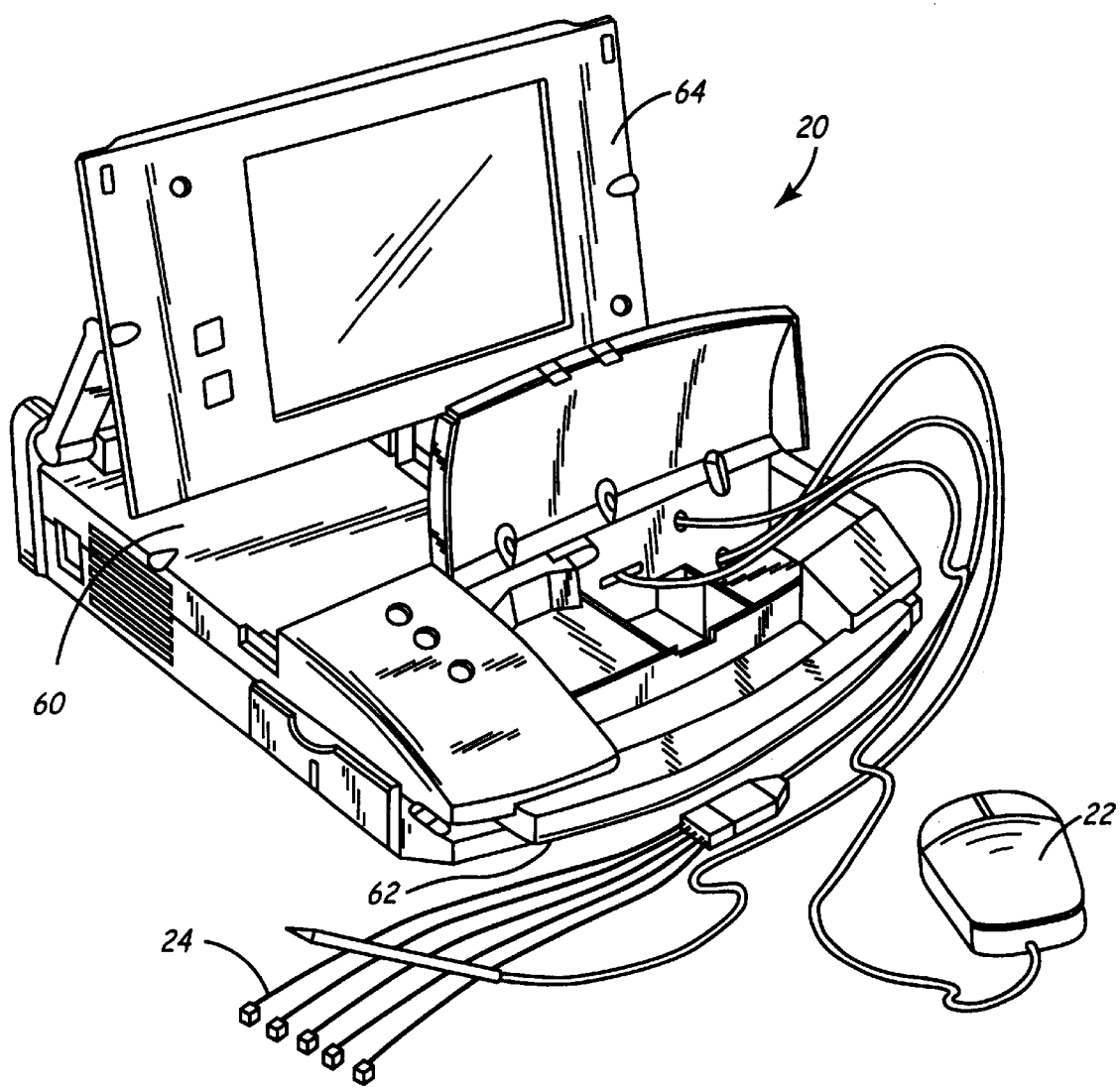
FIG. 2 is a perspective view of the external programming unit of FIG. 1.

In FIG. 2, there is shown a perspective view of programming unit 20 in accordance with the presently disclosed invention. Internally, programmer 20 includes a processing unit (not shown in the Figures) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 60, which is preferably made of thermal plastic or another suitably rugged yet relatively light-weight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

Those with ordinary skill in the art know it is often desirable to provide a means for determining the status of the patient's conduction system. Normally, programmer 20 is equipped with external ECG leads 24. It is these leads which are rendered redundant by the present invention.

In accordance with the present invention, programmer 20 is equipped with an internal printer (not shown) so that a hard-copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

Display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
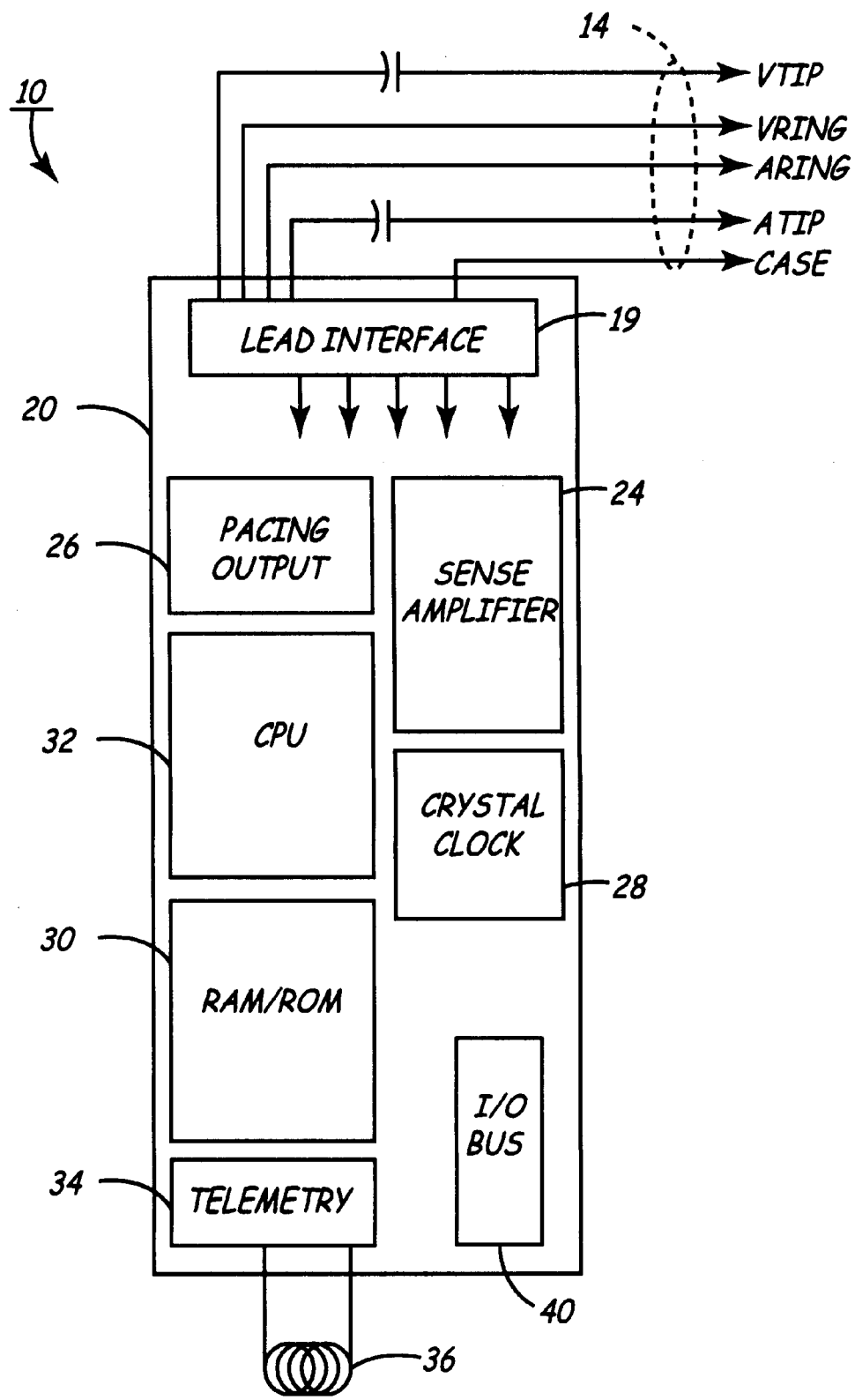
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 20 for controlling the device's pacing and sensing functions. The circuitry associated with stimulation control circuit 20 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 20 in FIG. 3 includes sense amplifier circuitry 24, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or micro controller, but in the present invention is a custom integrated circuit.

Although specific connections between CPU 32 and other components of stimulation control circuit 20 are not shown in FIG. 3, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator, provides main timing clock signals to stimulation control circuit 20. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 4:
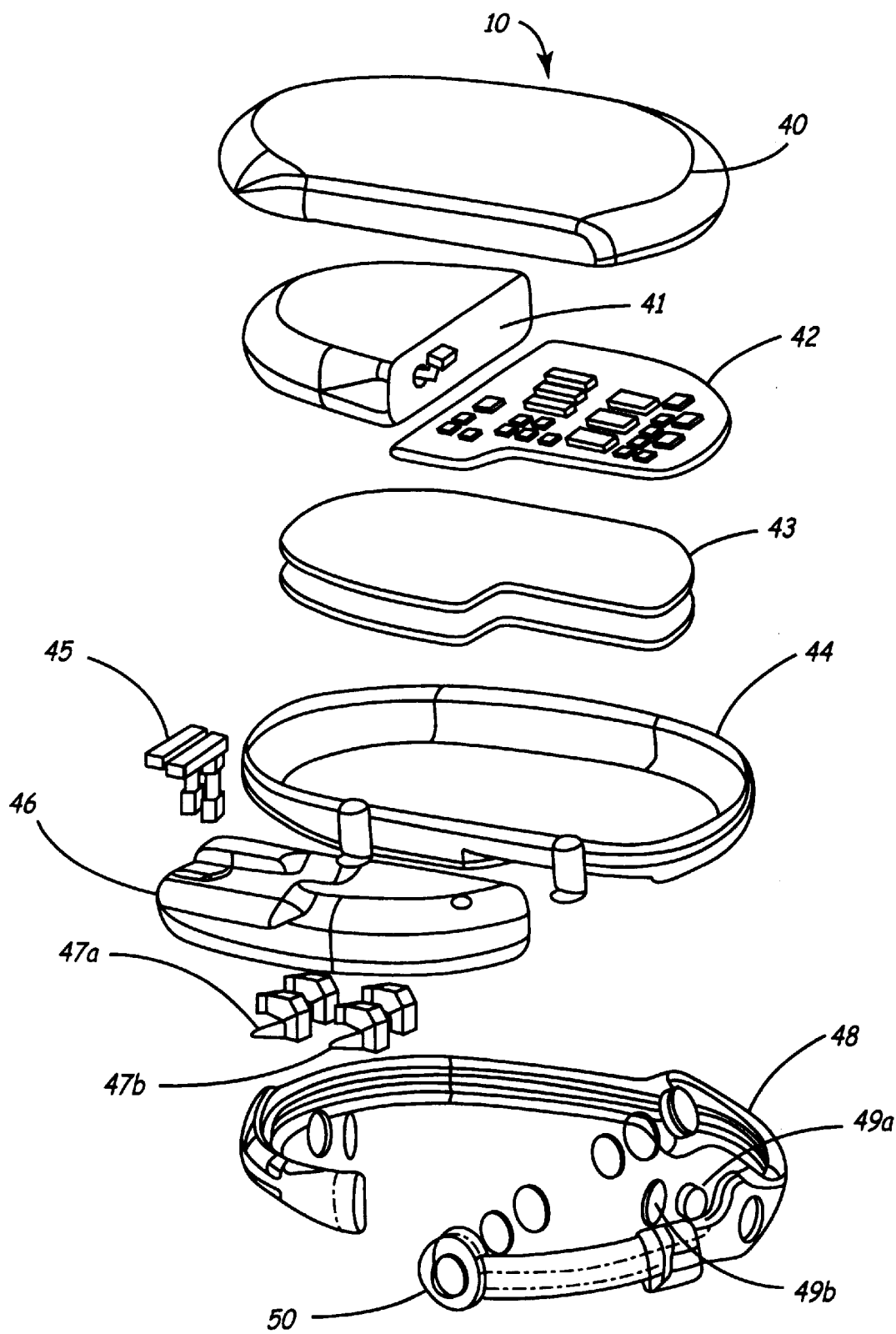
FIG. 4 is a breakaway drawing of a typical implantable cardiac pacemaker in which the present invention is practiced.

FIG. 4 is a breakaway drawing of a typical implantable cardiac pacemaker 10 in which the present invention is practiced. The outer casing of the pacemaker is composed of right shield 40 and left shield 44. Left shield 44 also has a feedthrough assembly through which wires electrically connecting the lead contacts 47a and 47b to hybrid circuitry 42 are passed. Power to circuitry 42 is provided by battery 41. Pacing leads (not shown) are inserted into lead connector module 46 so that the portion of the lead that leads to the lead ring electrode makes electrical contact with lead contact 47a and lead tip (distal) electrode makes electrical contact with lead contact 47b when lead fastener 46 is turned to its closed position.

Continuing with FIG. 4, the mechanical portion of the present invention consists of surround shroud 48 that is affixed circumferentially around the perimeter of the implantable pacemaker. In one embodiment of the present invention, there are four recessed openings 50. A cup 49a with a contact plate 49b is fitted into each recessed opening. Into each of recessed openings 50 is placed an electrode such as a helical electrode (see FIG. 9 for details) that, in conjunction with other paired electrodes detect cardiac depolarizations. These electrical signals are passed to contact plate 49b that is electrically connected to hybrid circuitry 42 via insulated wires running on the inner portion of surround shroud 48 (see FIG. 5 for details).

Figure 5:
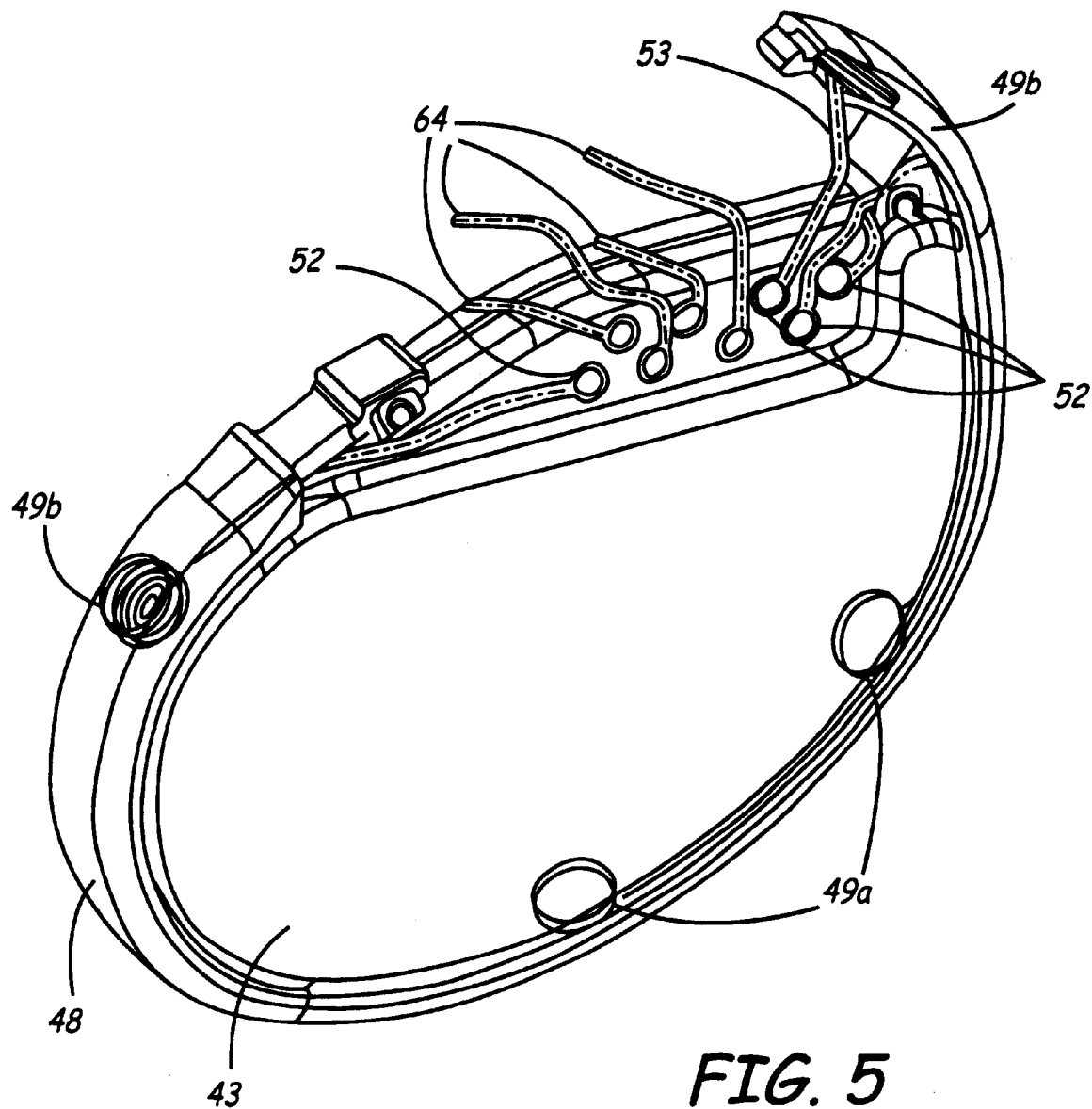
FIG. 5 is a sectional view of surround displaying electrical connections of the electrodes to the hybrid circuitry.

FIG. 5 is a sectional view of surround 48 displaying electrical connections of the electrodes to the hybrid circuitry surrounded by insulators 43. Surround displays recessed cups 49b and electrical contacts 49a all of which are connected to the hybrid circuitry (not shown) via tubular wiring 53. Tubular wiring 53 is connected to electrode contacts 52 located on upper portion of the board holding the hybrid circuitry. Other contacts 64 electrically connect the atrial and ventricular pacing lead tip and ring to the hybrid circuitry.

Figure 6:
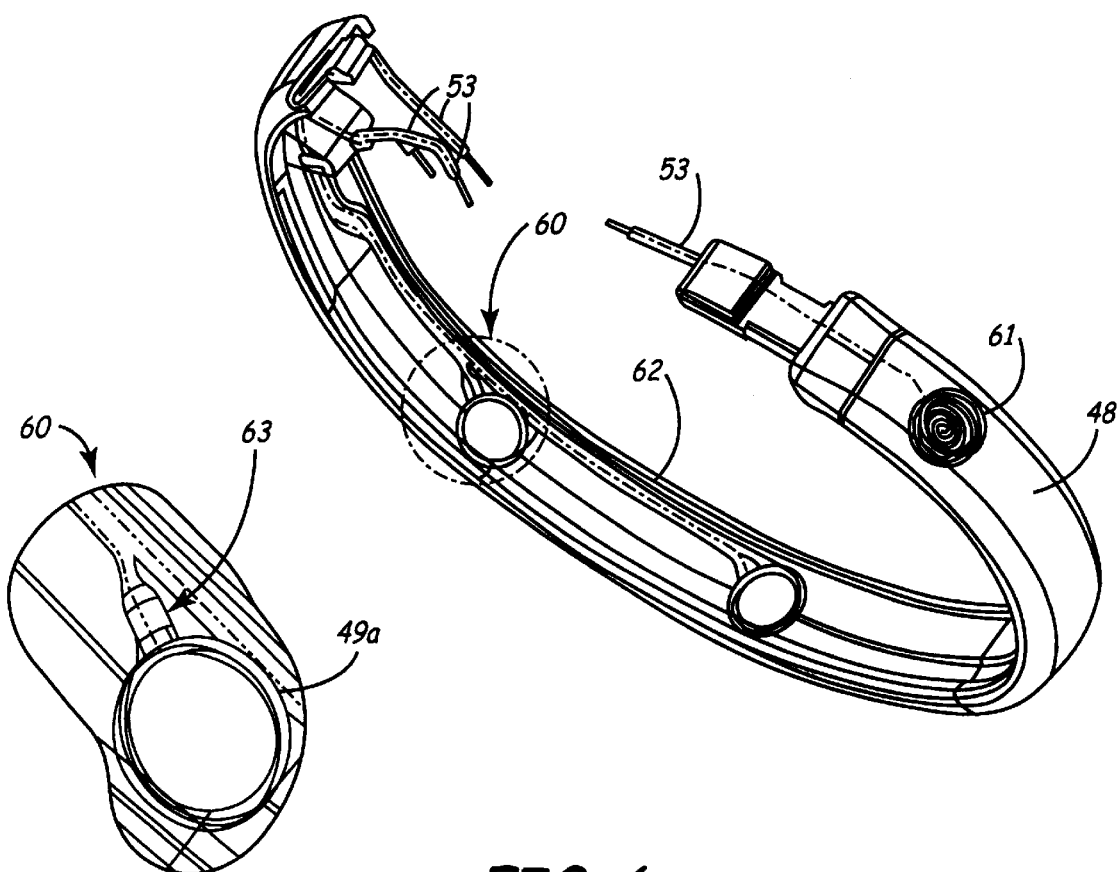
FIG. 6 is a sectional view of surround, prior to its fixation on the periphery of an implantable pacemaker.

FIG. 6 is a sectional view of surround shroud 48, prior to its fixation on the periphery of an implantable pacemaker. Detail 60 shows the bottom of recessed cup 49a into which electrode contact 49b (not shown) is placed. In one embodiment of the present invention, protruding end of coiled electrode 61 is placed into insulating connector 63 that is welded to tubular wiring 53. Tubular material wiring runs through channels 62 formed on the inside of the surround 48.

FIG. 7 is a cross sectional view of an electrode coil 61, which is one embodiment of an electrode practiced in the present invention. Helical coil 61 consists of a wire of platinum, platinum alloy, or any platinum group of metals whose surface may be treated by sputtering, platinization, ion milling, sintering, etching, or a combination of these processes to create a large specific surface area. Helical coil 61a is designed to fit into recessed cup 49b (see FIG. 5), within which helical coil 61b rests on electrical contact 49a (see FIG. 5). The protruding end of helical coil 61c does not require insulating connector 63 (see FIG. 6), because it is manufactured continuous with tubular wiring 53 (see FIG. 6).

Table 1 describes four electrode configurations that may be used in compliant shroud 48 (see FIG. 6) that may be fitted around an implanted pacemaker. Each column provides separation (in inches) that can be achieved between the electrodes for each configuration. These values will, of course, change depending on the shape and size of the implanted pacemaker (or other implanted medical device) being used. The data provided is typical for those implanted pacemakers in use today.

Using the values in Table 1 as reference points, one can estimate the relative signal amplitude detected by a pair of electrodes for a given angle of device orientation, as shown in Table 2.

FIG. 8 is an illustration of the various possible electrode sites that may be located along the perimeter of the implanted pacemaker within the compliant shroud. The spacing of the electrodes display the measurements depicted in Table 1. The spacings, as shown, also illustrate the vectors that may be used to detect the cardiac depolarizations. For example, the orthogonal 3-electrode design 302 requires only two potential vectors, as opposed to the equal spacing 3-electrode design 301 that may require the use of all three vectors. A more detailed analysis of these geometries may be found in P8552, Subcutaneous Electrode Array Virtual ECG Lead by Panken and Reinke, hereby referenced in its totality.

Turning now to Table 2, one can see the relative signal amplitudes for the different electrode. configurations given in Table 1. In general, as the number of electrodes increase, the magnitude of the detected cardiac signal increases. The underlying theory is based on several assumptions. 1) The implanted medical device and the SEA electrodes does not affect the corporeal electrical field(s). 2) The electrical field near the device is constant, with the result that the electrical field developed across a selected pair of electrodes is proportional to the electrical field, to the distance between the electrodes and, finally, proportional to the cosine of the angle between the electrical field vector and the line between the electrodes. 3) The device will be randomly oriented within the pocket relative to the electrical field. 4) The signal selected will be the largest.

In Table 2, the relative signal size is computed for each configuration using assumptions 3 and 4 above. These calculations are normalized to arbitrary electrical field strength of 1 mV/inch. (Note: this arbitrary choice is larger than is typically observed in humans or animals.)

As can be seen, the means signal amplitude increases as the number of electrodes increases. Also, if the electrode pairs have equal separation, the variation in signal amplitude is less affected by device orientation within the body. This last datum is vital because the implanting physician should be under no constraint as to how he or she implants the pacemaker within the body, assuming the device is implanted pectorally rather than abdominally. These trends in the relationship between signal amplitude and number of electrodes hold true as more electrodes are added. It does not, however, appear to be advantageous to use more than four electrodes, since the small improvements in signal amplitude would be achieved at the expense of increased device complexity, size, and cost.

FIG. 8 displays three individual and simultaneous ECG tracings taken during an acute study from a human patient, that is, temporarily attaching an implantable ventricularonly based pacemaker equipped with an SEA and a compliant shroud. The implantable ventricular lead had already been placed and meant for use with a currently available implantable pacemaker that was attached after the acute SEA study was completed.

The topmost ECG tracing is one taken from standard surface electrodes and labeled ECG II, that is, a tracing which uses ECG lead vector II (measured from left leg to left arm) to derive its data, a vector with which medical personnel, familiar with the art, are most comfortable. The shape of the ventricular depolarization waveform changes on the fourth complex. One might suspect that the pacemaker had just begun pacing on the implanted lead at this point and that full ventricular capture has occurred. Note, however, that the pacemaker artifact is missing from this and the remaining complexes on this ECG tracing. Such an omission makes it difficult to determine whether or not pacing is actually occurring.

Turning our attention now to the middle and bottommost tracings labeled SEA II and SEA III, we can see that these tracings taken from the pacemaker's SEA electrodes, provide information that might be impossible to gain from a surface ECG as depicted in ECG II. One familiar with reading ECGs could immediately note the differences between the four types of complexes noted on tracing SEA II and equally applicable to SEA III. The leftmost complex labeled Intrinsic has no pacemaker artifact (pacing output pulse) and so is easily identified as a normal, intrinsic ventricular depolarization or R-wave as would also be evident by comparing this complex to previous ones (not shown). On the other hand, although the next two complexes display pacemaker artifacts, the shape or morphology of the R-waves is exactly the same as the first waveform Intrinsic. These two waveforms are labeled Pseudofusion, that is, while there were pacing pulses, they fail to capture the ventricle. The third complex labeled Fusion shows an R-wave whose morphology has changed somewhat but is quite unlike those complexes labeled Capture. In these two complexes Pseudofusion, the pacing output pulse occurs at precisely the same time the intrinsic ventricular depolarization takes place. In neither case has the ventricle been completely captured. Finally, the last four complexes display full ventricular capture.

The importance of these data cannot be lightly dismissed. The evidence of full capture of the ventricle is vital to the implanting physician. Full capture following a pacemaker output pulse signals appropriate placement of the implanted lead(s), as well as an appropriate output setting of the implanted pacemaker. If one or the other is lacking, the health and safety of the pacemaker patient cannot be assured.

What is claimed is:

1. A cardiac data acquisition system including a leadless subcutaneous electrode array (SEA), the system comprising:
    a hermetically sealed case;
    a surround shroud including recesses into which electrodes are embedded; and
    signal processing circuitry inside the case being electrically coupled to the SEA to detect the cardiac signals.

2. The system of claim 1 wherein the periphery surface of the case is substantially flat.

3. The system of claim 1 wherein each electrode is a substantially flat multilayer ceramic electrode.

4. The system of claim 1 wherein said recesses are formed in clusters to contain a group of electrodes.

5. The system of claim 4 wherein said clusters include said recesses, each of which contain an individual electrode.

6. The system of claim 5 wherein signal to noise ratio is optimized using a set of four electrodes within said recesses.

7. An apparatus for leadless acquisition of electrocardiographic data comprising:
    a hermetically sealed implantable device case including a surround shroud having recesses;
    an array of cardiac depolarization sensing electrodes embedded into the surround shroud recesses along a peripheral edge surface of the case at locations providing maximal electrode spacing, the electrodes being sequentially coupled in one or more pairs to the terminals of one or more sense amplifiers; and
    means for storing signals from a selected electrode pair to determine a sensing vector that provides the largest cardiac signal.

8. The apparatus of claim 7 wherein said electrode spacing includes a spacing of two vectors with a separation angle equaled to 90° to thereby form octagonal spacing between electrode pairs for signal variation minimization.

9. The apparatus of claim 7 wherein said electrode spacing locates the electrodes in an equilateral triangle.

10. The apparatus of claim 9 wherein vectors are combined to provide adequate sensing of cardiac signals.

* * * * *